United States Patent [19]

Akamatsu

[11] Patent Number: 5,044,882

[45] Date of Patent: Sep. 3, 1991

[54] PRECESSIONAL CENTRIFUGAL PUMP

[75] Inventor: Teruaki Akamatsu, Nakadachiurimuromachi, Japan

[73] Assignee: Ube Industries, Ltd., Ube, Japan

[21] Appl. No.: 406,037

[22] Filed: Sep. 12, 1989

[30] Foreign Application Priority Data

Nov. 30, 1988 [JP] Japan .................................. 63-303576

[51] Int. Cl.$^5$ ............................................. F04D 29/40
[52] U.S. Cl. .................................. 415/182.1; 415/70; 415/206
[58] Field of Search ...................... 415/182.1, 183, 184, 415/203, 206, 207, 208.1, 70, 143, 900

[56] References Cited

U.S. PATENT DOCUMENTS

| | | | |
|---|---|---|---|
| 2,107,090 | 2/1938 | Swennes | 415/70 |
| 3,261,297 | 7/1966 | Daniel | 415/183 |
| 3,608,088 | 9/1971 | Dorman et al. | 415/206 |
| 3,647,314 | 3/1972 | Laessig | 415/206 |
| 4,389,159 | 6/1983 | Sarvanne | 415/206 |
| 4,722,660 | 2/1988 | Akamatsu | 415/70 |

Primary Examiner—John T. Kwon
Attorney, Agent, or Firm—Parkhurst, Wendel & Rossi

[57] ABSTRACT

A precessional centrifugal pump of the type adapted to deliver liquid while rotating it with an impeller that makes a precessional movement. The pump includes an annular space provided in a conical casing and an impeller arranged in the annular space in such a manner as to be able to run therein. The impeller includes of a head and a rod that extends through the opening of the casing at the apex thereof. The pump further includes a flow guide wall protruding from the center of the circular end face of the casing into the annular space and inwardly defining the annular space, an inlet way formed within the flow guide wall, and an outlet which extends tangentially from the annular space. The inlet way is open in a spiral manner from the head section of the flow guide wall over the entire length thereof.

3 Claims, 7 Drawing Sheets

A-A

B-B

C-C

D-D

PRECESSIONAL CENTRIFUGAL PUMP

BACKGROUND OF THE INVENTION

1. Field of the Invention

This invention relates to a precessional centrifugal pump, and more specifically, to a precessional centrifugal pump of the type which is adapted to deliver liquid while rotating it by means of an impeller making a precessional movement.

2. Description of the Related Art

The recent attempt to clinically utilize a light and compact centrifugal pump as a blood pump has attracted considerable attention. However, no conventional centrifugal pump can be rendered useful for purposes of this kind merely by diminishing its size since this would involve various problems such as the danger of germs and foreign matter entering it through the bearings and the sealing section as well as hemolysis (the destruction of red blood cells). In order to overcome these problems, a precessional centrifugal pump has been proposed. The impeller (head) of this centrifugal pump is not attached to a rotating shaft but to a rod which makes a precessional movement. The inventor of the present invention made an intense study of this type of centrifugal pump with a view to improving its efficiency and filed an international application on the subject (International Publication No. W086/04962).

The object of the international application was to provide a precessional centrifugal pump which exhibits a high efficiency and which can effectively prevent hemolysis. FIGS. 5 and 6 show a centrifugal pump in accordance with this international application.

As shown in the drawings, a centrifugal pump 9 exhibits a casing 2 having a conical inner configuration and an annular space 3. The casing 2 has a side wall 2a and an opening 2b provided at the apex thereof. Outwardly, the annular space 3 is defined by the side wall 2a of the casing 2, and, inwardly, by a flow guide wall 7 which extends from the center of the circular end face of the casing 2 into the annular space 3.

The annular space 3 is connected through an inlet way 8 to an inlet 10 provided at the center of the circular end face of the casing 2. The inlet way 8 is a spiral flow passage extending through the flow guide wall 7. The annular space 3 is further connected to an outlet 5 which extends tangentially from that section of the side wall 2a of the casing 2 which faces the inlet way 8 (This section expands smoothly on the outside).

An impeller 6 comprising a head 9 and a rod 14 is arranged in the annular space 3 in such a manner as to be able to run therein. The head 9 of the impeller 6 consists of a conical end section 9a and a base section 9b. The impeller 6 extends in the annular space 3 along the side wall 2a of the casing 2 and along the flow guide wall 7. The rod 14 extends through the opening 2b of the casing 2 to the exterior of the annular space 3.

The opening 2b is covered with a sealing membrane 15 made of a flexible material withstanding repeated bending, such as polyurethane or silicone. The sealing membrane 15 is attached to the side wall 2a of the casing 2 as well as to the impeller 6 in a water-tight manner. The rod 14 of the impeller 6, extending out of the annular space 3, is attached to a supporting member 17 through a bearing 18, the supporting member 17, when rotated, causing the impeller 6 to make a precessional movement around the opening 2b. The supporting member 17 is connected to the shaft of a motor (not shown) and is rotated thereby.

With this precessional centrifugal pump turbulence of flow, etc. in the pump chamber can be prevented to a certain degree, with the pumping efficiency being improved to around 40%.

However, the performance of this prior art pump is still less than perfect. Besides, the problem of hemolysis remains.

SUMMARY OF THE INVENTION

In view of this, the inventor of the present invention made a further study of the subject and improved the configuration of the pump inlet. He went on to examine the configuration of the pump outlet, the impeller head, etc., finally achieving the present invention.

In accordance with this invention, there is provided a precessional centrifugal pump of the type comprising: a conical casing having a side wall, a circular end face and an opening at the apex thereof; an annular space which is outwardly defined by the side wall of the above-mentioned conical casing; an impeller which is arranged in the above-mentioned annular space in such a manner as to be able to run therein and which consists of a head and a rod that extends through the opening at the apex of the above-mentioned casing; a flow guide wall protruding from the center of the circular end face of the above-mentioned casing into the above-mentioned annular space and inwardly defining the above-mentioned annular space; an inlet way formed within the above-mentioned flow guide wall; an inlet provided at the center of the circular end face of the casing and connected to the above-mentioned annular space through the above-mentioned inlet way; an outlet tangentially extending from the above-mentioned annular space; and a sealing membrane covering the above-mentioned opening and adhering to the side wall of the casing and the above-mentioned impeller in a water-tight manner. The above-mentioned inlet way is open in a spiral manner from the head section of the flow guide wall over the entire length thereof.

Because of the above-described structure in which the inlet way of the pump is open in a spiral manner from the head section of the flow guide wall over the entire length thereof, this precessional centrifugal pump can provide a larger liquid inflow area than in the prior art, and the pumping effect of the impeller rod can also be utilized.

If, in the precessional centrifugal pump of this invention, the outer periphery of the outlet tangentially extending from the annular space, exhibits a smooth expansion which is convex in the direction reverse to the flow whirl, the generation of a vortex at this position due to the fluid portion with a higher potential energy (the portion at the position where the whirl radius is relatively large) mixing with the fluid portion with a lower potential energy can be prevented, and the flow can be homogenized.

Further, it is advantageous if, in this precessional centrifugal pump, the impeller head has a club-like configuration since a whirling energy can then be imparted to the fluid entering the pump.

BRIEF DESCRIPTION OF THE DRAWINGS

FIGS. 1(a) to 1(f) pertain to an embodiment of the precessional centrifugal pump of this invention, of which:

FIG. 1(a) is sectional view of the inlet section of the precessional centrifugal pump;

FIG. 1(b) is a perspective view of its inlet way;

FIGS. 1(c) to 1(f) are sectional views taken along the lines A—A, B—B, C—C and D—D of FIG. 1(a), respectively;

DETAILED DESCRIPTION OF THE PREFERRED EMBODIMENTS

The present invention will now be described in detail with reference to the embodiments shown in the accompanying drawings. This invention should not be construed as restricted to these embodiments.

The following description of the preferred embodiments will be given in contrast with the conventional pump structure shown in FIGS. 5 and 6, focusing on the differences between this invention and the prior art.

FIGS. 1(a) to 1(f) show an embodiment of the precessional centrifugal blood pump of this invention. This embodiment differs from the conventional pump in the structure of the inlet way 8 provided in the flow guide wall 7.

Figure 1A:
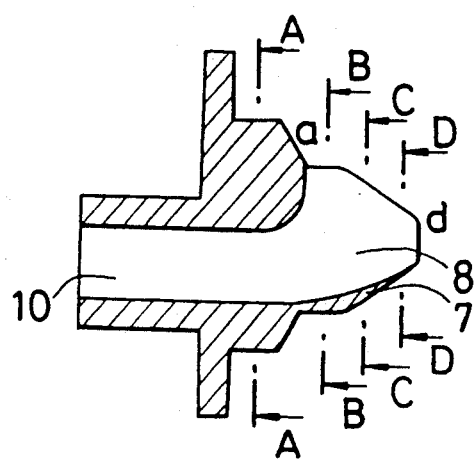
Figure 1B:
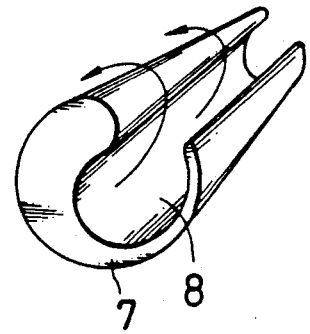

In accordance with this embodiment, the inlet way 8 is open in the spiral manner from the head section d of the flow guide wall 7 over the entire length (from a to d in FIG. 1(a)) of this guide wall. Accordingly, the pump provides a wider inflow area for blood and allows the pumping effect of the rod 14 of the impeller 6 to be utilized, thereby improving the performance of the pump as a whole.

Figure 2:
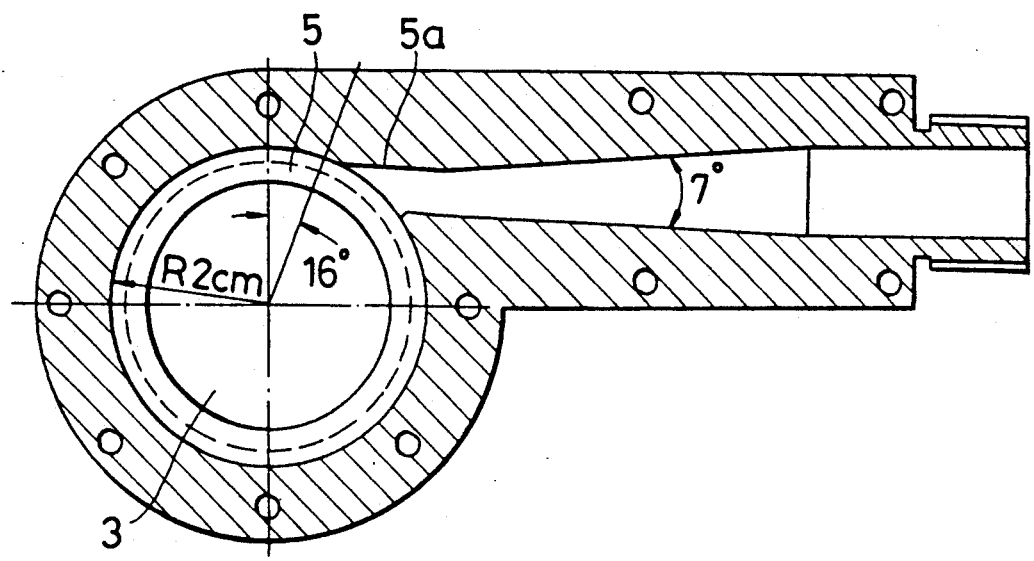
FIG. 2 is a sectional view taken along a plane perpendicular to the pump axis, showing the outlet configuration of the pump.
Figure 3:
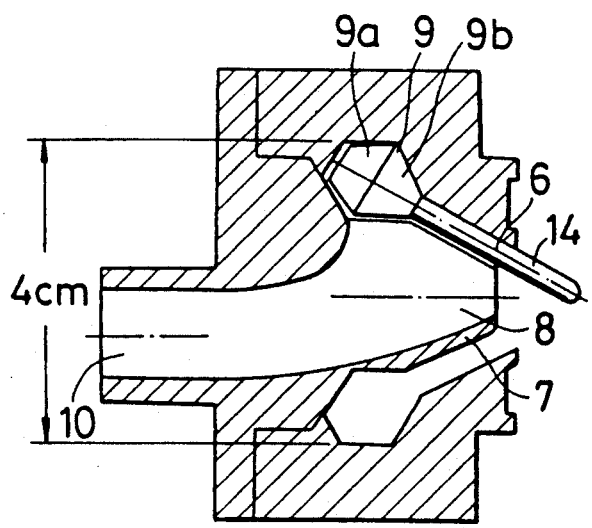
FIGS. 3 and 4 are axial sectional views of other embodiments of this invention.

FIGS. 2 and 3 show another embodiment of the pump of this invention. In this embodiment, an improvement has been achieved in the structure of the pump outlet 5. In the conventional pump, the outlet 5 extends tangentially from the side wall 2a of the pump casing 2 which swells smoothly outwards, whereas, in this embodiment, the outer peripheral section 5a of the outlet 5, tangentially extending from the annular space 3, is designed to exhibit a smooth expansion which is convex in the direction reverse to that of the whirling.

Various experiments have shown that this configuration helps to prevent the generation of a vortex at this position formerly due to the outer peripheral fluid portion with a higher potential energy mixing with the inner peripheral fluid portion with a lower potential energy, and that further flow homogenization can be achieved.

It is desirable that the outlet 5 have a diffuser-configuration in which its section augments as it extends away from the annular space 3, the diffuser expansion angle being preferably in the range 7 to 8 degrees. This arrangement is advantageous in that it allows the liquid in the annular space 3 to enter the outlet 5 smoothly, with the pressure loss being reduced.

Figure 4:
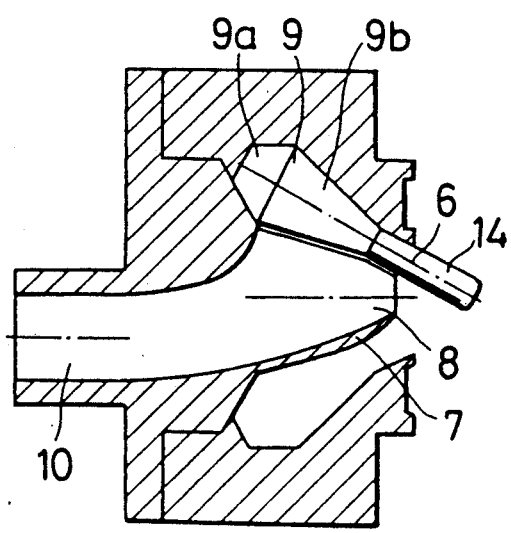

FIG. 4 shows still another embodiment of the pump of this invention. In this embodiment, the head 9 of the impeller 6 has a club-like configuration. Specifically, this is realized by augmenting the height of the truncated cone constituting the base section 9b of the impeller head 9.

With this club-like configuration of the impeller 9, it is possible to gradually impart a whirling energy to the fluid in the annular space 3 of the pump when it is led to the outlet 5, whereby the pump efficiency can be enhanced.

In the following, the results of experiments conducted on the pumps of this invention as well as a conventional one will be described.

Embodiment 1

Figure 5:
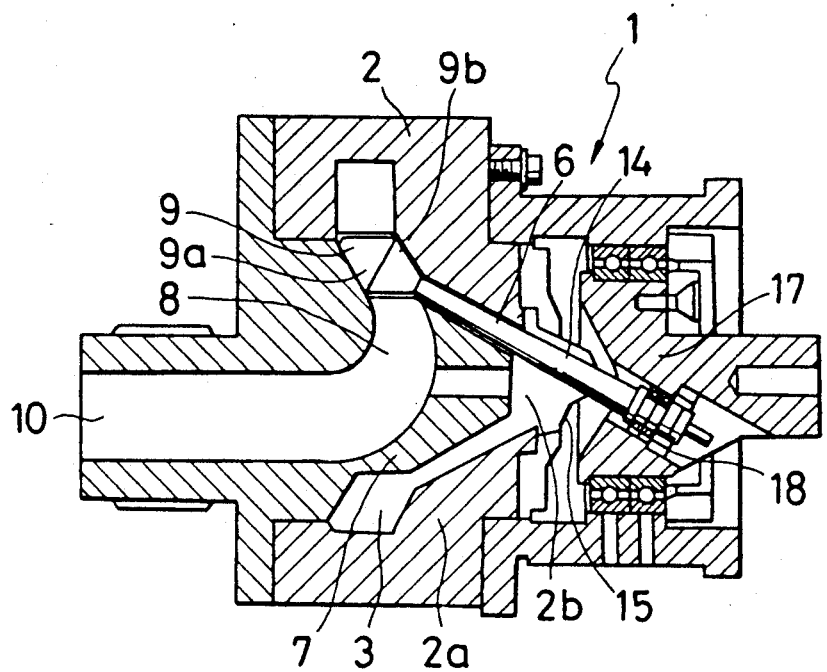
FIG. 5 is a sectional view, taken along an axial plane, of a conventional precessional centrifugal pump.
Figure 6:
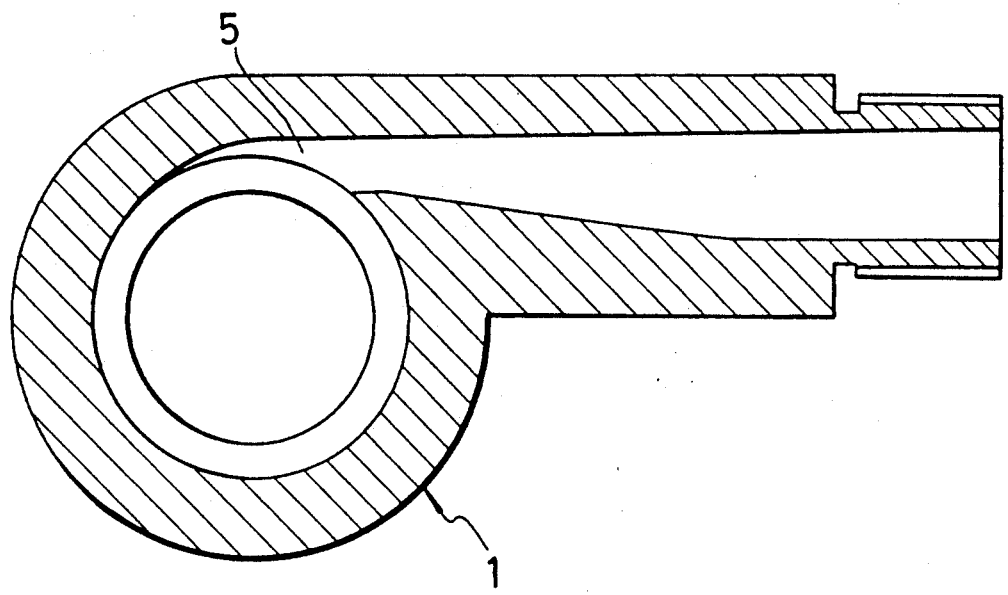
FIG. 6 is a sectional view, taken along a plane perpendicular to the axis, of the conventional pump.

The characteristics of the pumps in accordance with this invention, shown in FIGS. 1 to 4, and those of the conventional pump shown in FIGS. 5 and 6 were examined so as to compare their performances with each other. The dimensions of the pumps examined were as follows:

Pump I of this Invention (FIG. 1)

Figure 7:
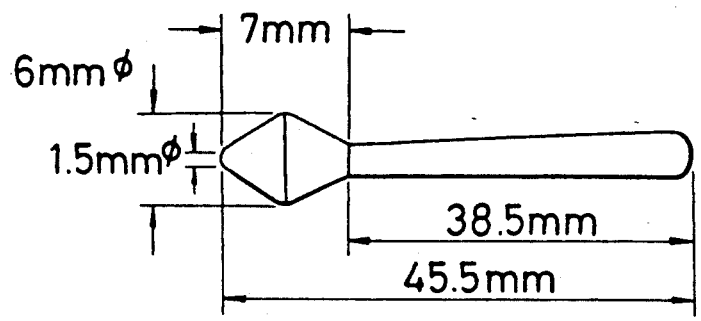
FIGS. 7 to 9 are dimensional drawings showing the dimensions of the respective impellers of the first to third embodiments of the pump of this invention.

Impeller: the dimensions shown in FIG. 7

Outer peripheral rotating radius $R_2$ of the impeller: 2 cm

Figure 1C:
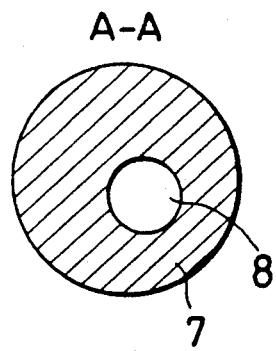

Inlet way formed in the flow guide wall:

Outer diameter of the section in FIG. 1(c) ... 30 mm$\phi$

Figure 1D:
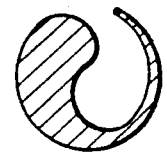

Outer diameter of the section in FIG. 1(d) ... 20 mm$\phi$

Figure 1E:
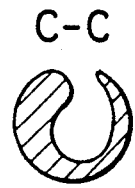

Outer diameter of the section in FIG. 1(e) ... 1.7 mm$\phi$

Figure 1F:

Outer diameter of the section in FIG. 1(f) ... 12 mm$\phi$

Inner peripheral diameter of the section in FIG. 1(c) ... 11 mm$\phi$

Inner peripheral diameter of the section in FIG. 1(d) ... 10 mm$\phi$

Inner peripheral diameter of the section in FIG. 1(e) ... 9 mm$\phi$

Inner peripheral diameter of the section in FIG. 1(f) ... 7 mm$\phi$

Pump II of this Invention (FIGS. 2 and 3)

Figure 8:
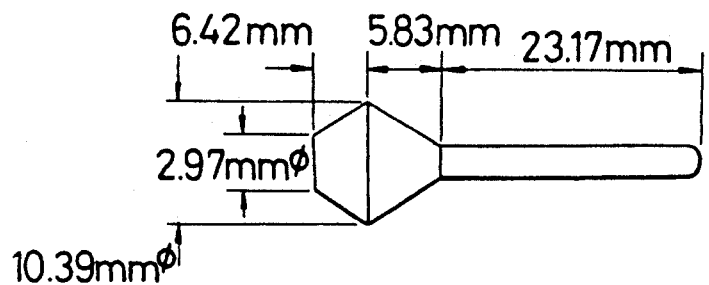

Impeller: the dimensions shown in FIG. 8

Outlet configuration: As shown in FIG. 2, the outlet was formed so that it exhibited a smooth expansion extending from point A that deviated 16 degrees from the central axis of the pump and was convex in the direction reverse to the fluid whirl, the swell having a curvature diameter of 50 mm. The expansion angle of the outlet diffuser was 7 degrees.

The radius of rotation around the impeller and the inlet way formed in the flow guide wall were the same as those in Pump I of this invention.

Pump III of this Invention (FIG. 4)

Figure 9:
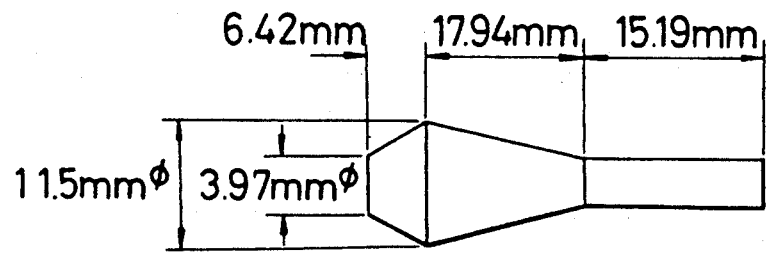

Impeller: the dimensions shown in FIG. 9 Other aspects of this pump are the same as those of Pump II of this invention.

Pump IV (the conventional pump shown in FIGS. 5 and 6)

The impeller of the pump is the same as that of Pump 1 in accordance with this invention.

Radius of rotation R₂ of the outer periphery of the impeller: 2 cm

Inlet way formed in the flow guide wall:

The same as that shown in FIG. 1 except for the fact that it is not open in a spiral manner from the head section of the flow guide wall over the entire length thereof, but is open only partially.

Figure 10:
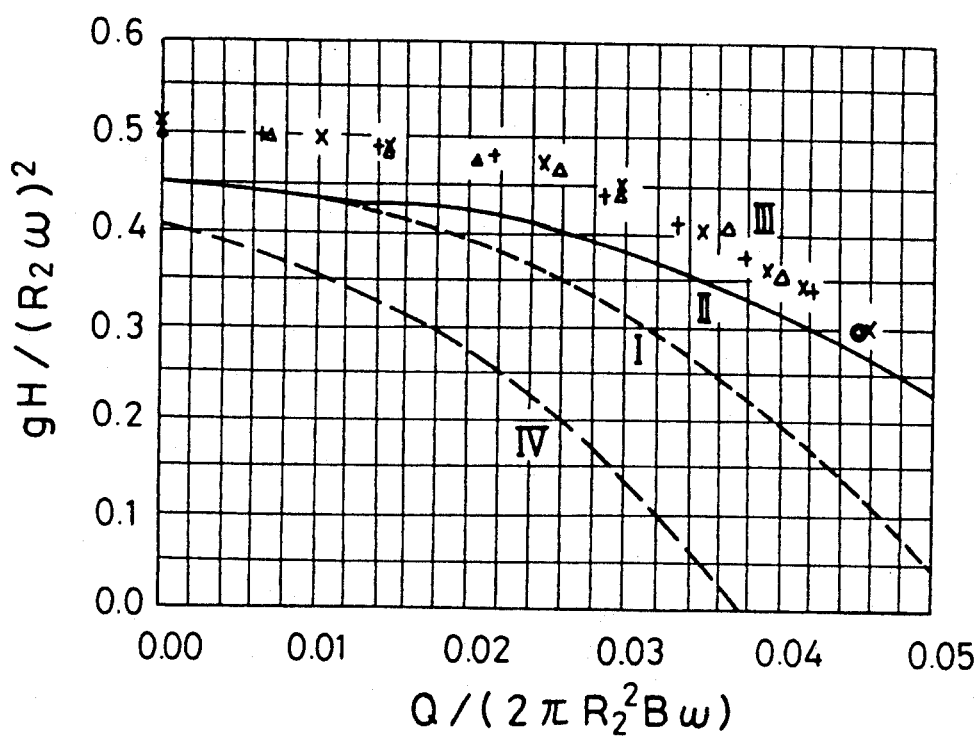
FIG. 10 is a graph showing dimensionless pressure/flow-rate pump characteristics.
Figure 11:
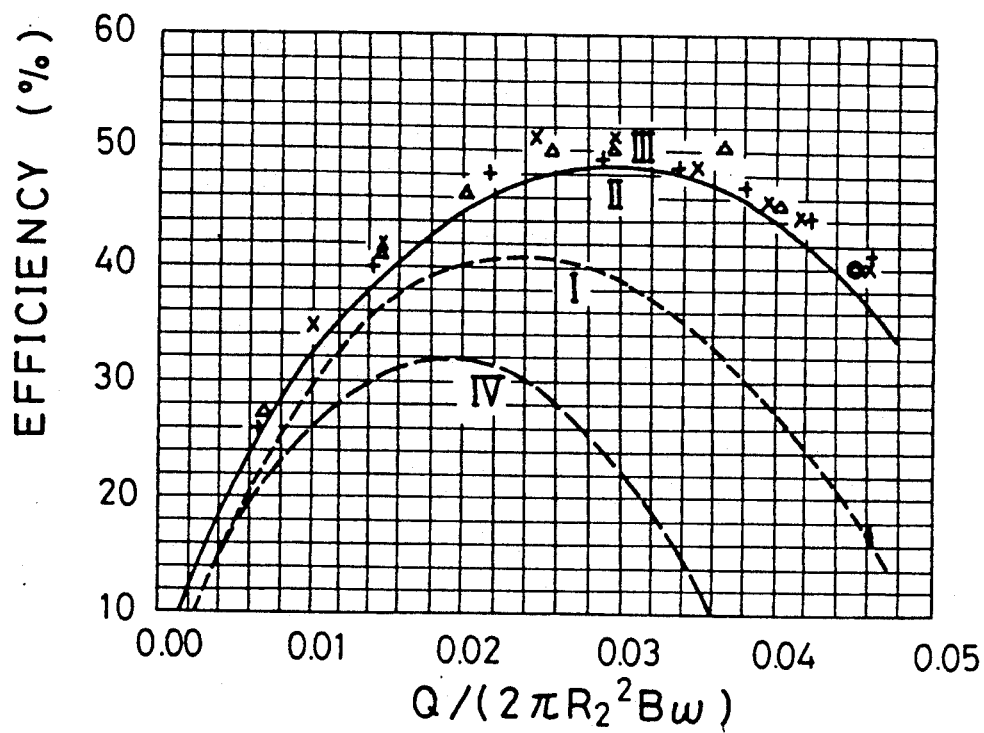
FIG. 11 is a graph showing dimensionless flow-rate/efficiency pump characteristics.
Figure 12:
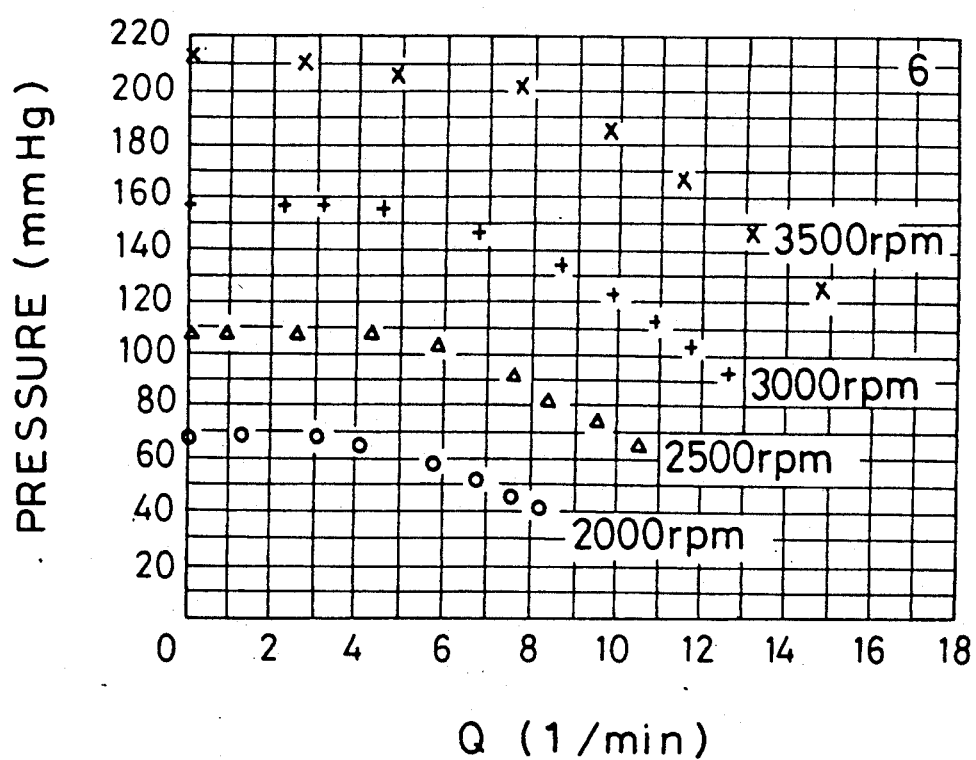
FIG. 12 is a graph showing the pressure/flow-rate characteristics of the third embodiment of the pump of this invention at different pump speeds.
Figure 13:
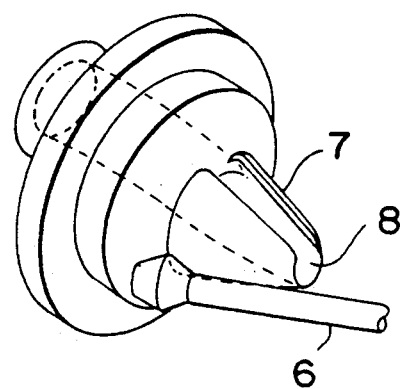
FIG. 13 is a perspective view of the invention.
Figure 14:
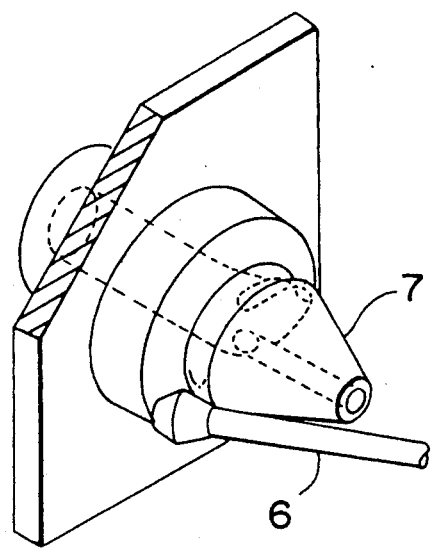
FIG. 14 is a perspective view of the prior art.

The graphs of FIGS. 10 to 12 show the results of examinations conducted of the characteristics of the above pumps.

FIG. 10 shows the dimensionless pressure/flow-rate characteristics of these pumps, and FIG. 11 shows dimensionless flow-rate/efficiency characteristics thereof. The broken line, the dotted line, the solid line, and the plot line represent the characteristics of Pump IV (the conventional pump), Pump I, Pump II, and Pump III, respectively.

FIG. 12 shows pressure/flow-rate characteristics of Pump III at different pump speeds (2000, 2500, 3000 and 3500 rpm).

The reference characters in FIGS. 10 to 12 indicate the following quantities: Q: flow rate; R₂: outer turning periphery radius of the impeller; B: impeller width; ω: angular velocity; g: acceleration; H: head.

As will be appreciated from the above results, the pumps of this invention manifest an improvement in characteristics over the conventional pump, i.e., Pump IV. The improvements ranking in the ascending order were: Pump I, Pump II and Pump III. In particular, Pump III exhibited over a wide flow-rate range a dimensionless pressure of $gH/(R_2\omega)^2 = 0.5$, the maximum value that is possible in a centrifugal pump. Thus, the pump of this invention has realized an improvement in efficiency of approximately 50% at its maximum.

Furthermore, because of the improvement in the pressure/flow-rate characteristic, the pump of this invention can generate a high pressure at a lower speed than in the prior art. Thus, Pump III, for example, makes it possible to attain an operating point with a pump-out flow rate of 6 l/min. and a pressure of 10 mmHg with a speed of 2500 rpm, whereas the conventional pump, Pump IV, requires 3000 rpm to attain the same operating point.

Thus, because of its heightened efficiency, the pump of this invention helps to reduce the energy consumed in moving the blood. In addition, because of its lowered impeller speed, the pump of this invention makes it possible to diminish the shearing stress. A synergetic effect derived from these properties allows hemolysis to be mitigated.

As described above, this invention provides the following advantages:

First, the precessional centrifugal pump of this invention has a specific inlet way configuration which results in a wider liquid inflow area, allowing the pumping effect of the impeller rod to be utilized, which enhances the pump efficiency.

Second, the outer periphery of the outlet of the precessional centrifugal pump of this invention may exhibit a smooth expansion which is convex in the direction reverse to that of the flow whirling, thereby preventing the generation of a vortex in the outlet section and homogenizing the flow.

Third, the impeller head of the precessional centrifugal pump of this invention may have a club-like configuration, which will make it possible to impart a whirling energy to the liquid entering the pump, thereby enhancing the pump efficiency.

What is claimed is:

1. A precessional centrifugal pump comprising:
   a conical casing having a side wall, a circular end face and an opening at an apex of said casing;
   an annular space which is externally defined by the side wall of said casing;
   an impeller which is arranged in said annular space so as to revolve therein and which consists of a head and a rod that extends through the opening at the apex of said casing;
   a flow guide wall protruding from the center of the circular end face of said casing into said annular space and having a head section which partially internally defines said annular space;
   an inlet way formed within said flow guide wall and being open axially in a spiral manner along an entire length of said head section of said flow guide wall;
   an inlet provided at the center of the circular end face of said casing and connected to said annular space through said inlet way;
   an outlet tangentially extending from said annular space; and
   a sealing membrane covering said opening at the apex of said casing, said membrane adhering to the side wall of said casing and to said impeller in a watertight manner.

2. The precessional centrifugal pump of claim 1, wherein said outlet tangentially extending from said annular space exhibits a smooth expansion.

3. The precessional centrifugal pump of claim 1, wherein the head of said impeller has a club-like configuration.

* * * * *